US00PP28658P3

(12) United States Plant Patent
Radler

(10) Patent No.: US PP28,658 P3
(45) Date of Patent: Nov. 21, 2017

(54) GRANDIFLORA ROSE PLANT NAMED 'RADNECTAR'

(50) Latin Name: *Rosa hybrida*
Varietal Denomination: cv. Radnectar

(71) Applicant: THE CONARD-PYLE COMPANY, West Grove, PA (US)

(72) Inventor: William J. Radler, Greensfield, WI (US)

(73) Assignee: THE CONRAD-PYLE COMPANY, West Grove, PA (US)

( * ) Notice: Subject to any disclaimer, the term of this patent is extended or adjusted under 35 U.S.C. 154(b) by 19 days.

(21) Appl. No.: 14/756,687

(22) Filed: Sep. 30, 2015

(65) Prior Publication Data

US 2017/0094848 P1 Mar. 30, 2017

(51) Int. Cl.
*A01H 5/02* (2006.01)

(52) U.S. Cl.
USPC ..... Plt./135

(58) Field of Classification Search
USPC ..... Plt./135, 136, 130, 146, 147, 106, 105
See application file for complete search history.

*Primary Examiner* — June Hwu
(74) *Attorney, Agent, or Firm* — Bucnanan Ingersoll & Rooney PC

(57) ABSTRACT

A new and distinct Grandiflora rose plant is provided that abundantly and substantially continuously forms attractive single cup-shaped bright orange to apricot blossoms. The plant exhibits vigorous vegetation and an upright and bushy growth habit. The foliage is ornamental dark green with a glossy finish on the upper surface. The light blossom coloration contrasts nicely with the dark green foliage. The disease resistance is excellent, particularly with respect to black spot, rust and mildews. The plant is well suited for providing attractive ornamentation in in the landscape.

2 Drawing Sheets

Botanical/commercial classification: *Rosa hybrida*/Grandiflora Rose Plant.

Varietal denomination: cv. Radnectar.

SUMMARY OF THE INVENTION

The new variety of *Rosa hybrida* Grandiflora rose plant of the present invention was created in June 2001 at Greenfield, Wis., U.S.A., by artificial pollination wherein two parents were crossed which previously had been studied in the hope that they would contribute the desired characteristics. The female parent (i.e., seed parent) was the 'Harwelcome' variety (U.S. Plant Pat. No. 9,161), and the male parent (i.e., pollen parent) was the unreleased 'Radorg' variety (non-patented in the United States). The parentage can be summarized as follows:

'Harwelcome'×Radorg'.

The seeds resulting from the above pollination were sown and small plants were obtained which were physically and biologically different from each other. Selective study resulted in the identification of a single plant of the new variety.

It was found that the new Grandiflora rose plant of the present invention possesses the following combination of characteristics:

(a) abundantly and substantially continuously forms attractive single cup-shaped bright orange to apricot blossoms,
(b) exhibits an upright and bushy growth habit,
(c) forms vigorous vegetation,
(d) forms attractive ornamental dark green foliage with a glossy finish on the upper surface that contrasts well with the blossom coloration, (e) exhibits excellent disease resistance particularly with respect to black spot, rust and mildews, and
(f) is well suited for providing attractive ornamentation in the landscape.

A new rose variety is provided that displays attractive bright orange to apricot colored blossoms, a dense upright and bushy growth habit, and excellent disease resistance. The foliage has been observed to remain exceptionally clean even under tough, hot and humid growing conditions The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors upon an inspection of the blossoms. More specifically, the 'Radwelcome' variety forms dissimilar double blossoms having approximately 25 to 30 petals, and the 'Radorg' variety displays a dissimilar climbing growth habit.

The new variety also can be readily distinguished from the 'Meiludere' variety (U.S. Plant Pat. No. 18,707) which exhibits dissimilar pink blossoms with some light salmon coloration.

The characteristics of the new variety have been found at Wasco, Calif., U.S.A., to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radnectar', and will be marketed under the HONEY NECTAR trademark.

BRIEF DESCRIPTION OF THE PHOTOGRAPHS

The accompanying photographs show, as nearly true as it is reasonably possible to make the same in color illustrations of this character, typical specimens of the new variety. The illustrated rose plants of the new variety were approximately three years of age and were observed during May 2011 while growing outdoors on its own roots at West Grove, Pa., U.S.A.

DETAILED BOTANICAL DESCRIPTION

Figure 1:
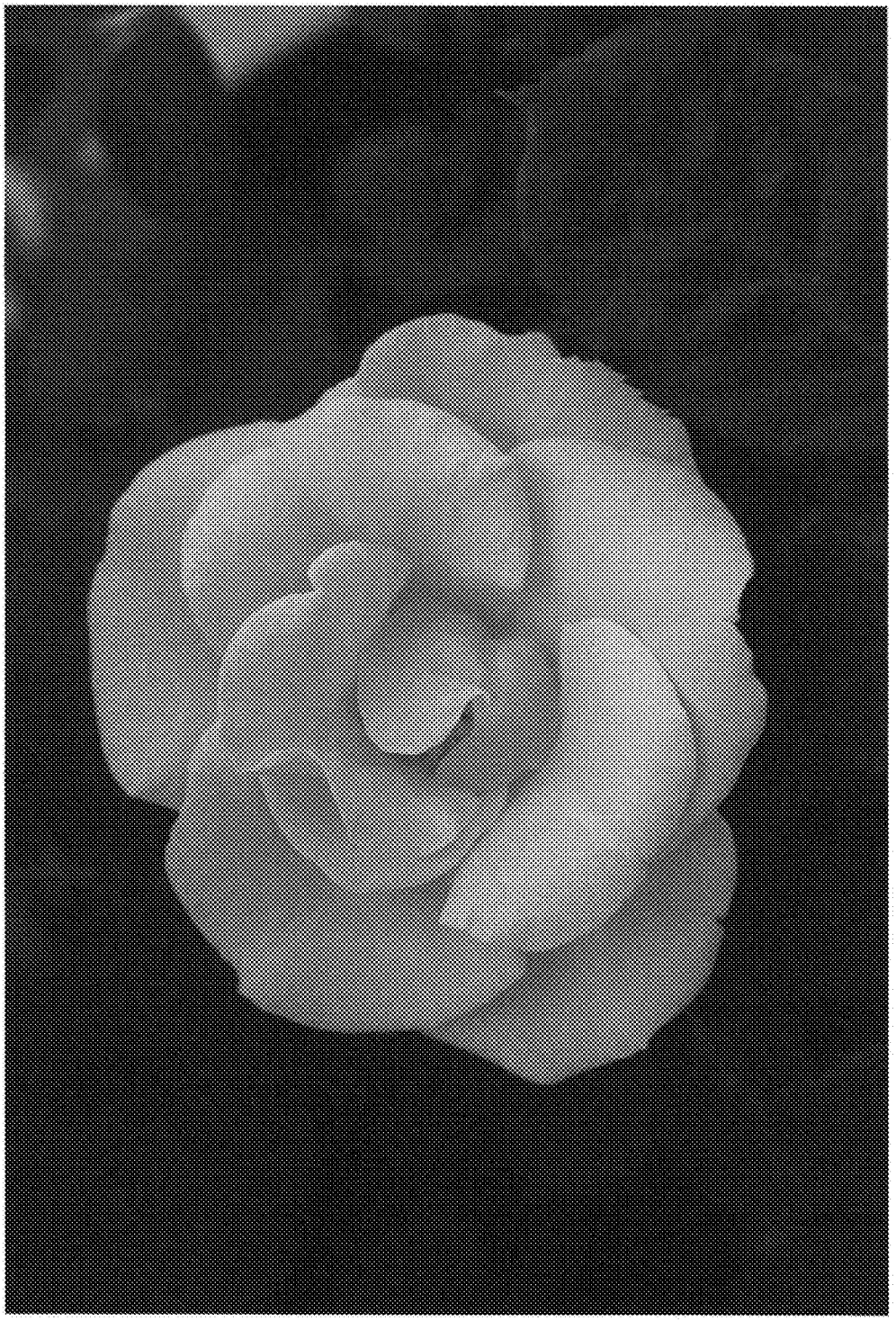
FIG. 1 shows a close enlarged view of a typical attractive open blossom of the new variety.
Figure 2:
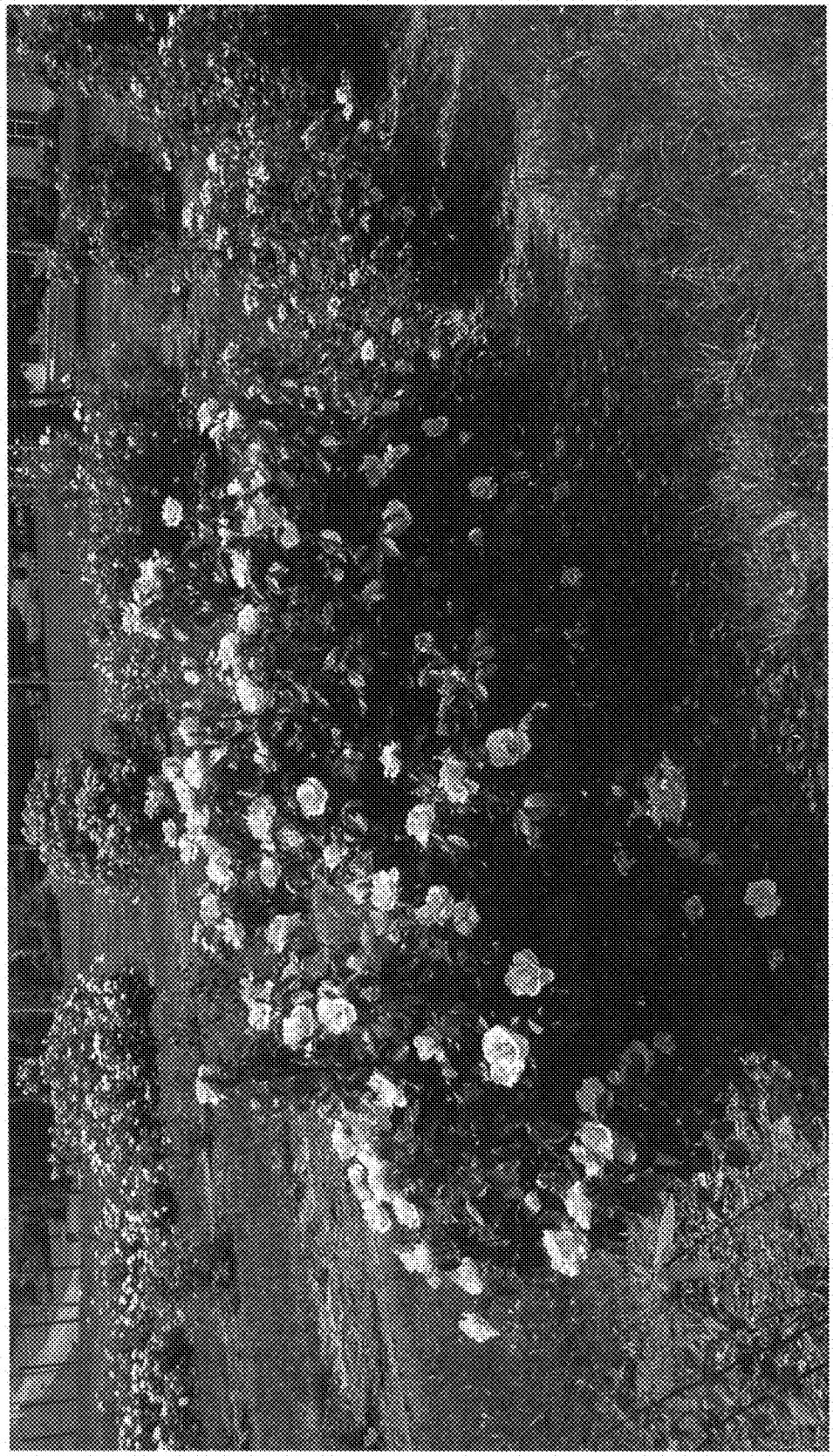
FIG. 2 shows a row of flowering plants of the new variety while growing in full sun. The upright and bushy growth habit is depicted.

The chart used in the identification of colors is that of The Royal Horticultural Society (R.H.S. Colour Chart—1995 Edition), London, England. The description is based on the observation of two-year-old specimens of the new variety during August while growing in containers on their own roots at West Grove, Pa., U.S.A.

Class: Grandiflora Rose. Variety 'Radnectar'.

Plant:

*Height*.—Commonly approach approximately 1.5 m on average at maturity.

*Width*.—Commonly approach approximately 90 cm on average at maturity.

*Habit*.—Upright and bushy.

Branches:

*Length*.—Main stems commonly approximately 8 cm on average, and secondary stems commonly approximately 27 cm on average.

*Color*.—Near Yellow-Green Group 144A on young stems, and commonly near Yellow-Green Group 146A mixed with some Greyed-Brown Group 199A for old wood.

*Anthocyanin*.—Commonly moderate on young shoots.

*Thorns*.—Size: commonly approximately 1.1 cm in length on average and approximately 7 mm in width on average at the point of attachment when young, and approximately 9 mm in length on average and approximately 5 mm in width on average at the point of attachment when mature. Color: commonly near Yellow-Green Group 152D on young stems, and near Greyed-Orange Group 177B when mature.

Leaves:

*Size*.—Commonly approximately 12 cm in length on average, and approximately 8 cm in width on average for a five-leaflet leaf.

*Stipules*.—Length: approximately 1.3 cm on average. Width: approximately 6.0 mm on average. Color: commonly near Yellow-Green Group 144A highlighted on inner margins by near Greyed-Purple Group 184A.

*Petioles*.—Length: approximately 2.5 cm on average. Diameter: approximately 2.0 mm on average. Surface texture: aculeolate. Upper surface color: commonly near Yellow-Green Group 144A with highlights near Greyed-Purple Group 184A. Lower surface color: commonly near Yellow-Green Group 144A.

*Rachis*.—Length: approximately 3.5 cm on average. Diameter: approximately 2.0 mm on average. Surface texture: aculeate to aculeolate. Upper surface color: commonly near Yellow-Green Group 144A with highlights near Greyed-Purple Group 184A. Lower surface color: commonly near Yellow-Green Group 144A.

*Leaflets*.—Number 3, 5, and 7. Length: approximately 5.5 cm on average for a terminal leaflet, and approximately 4 cm on average for a lower leaflet. Width: approximately 3.5 cm on average for a terminal leaflet, and approximately 2.5 cm on average for a lower leaflet. Shape: generally ovate with an acute apex and rounded base. Margins: serrate. Texture: generally smooth on the upper and under surfaces. Overall appearance: attractive dark green leaves with a glossy upper surface. Color: (when young): Upper surface: near Green Group 137A. Under surface: near Green Group 137C. Color (when fully mature): Upper surface: near Green Group 139A. Under surface: near Green Group 139C.

Inflorescence:

*Number of flowers*.—Commonly singly or in a cluster of approximately 2 to 4 blossoms per stem on average.

*Peduncle*.—Near Yellow-Green Group 144A in coloration, commonly approximately 3.5 cm in length on average, approximately 2.5 mm in diameter on average, and commonly sparsely covered with small flexible thorns less than 2 mm in length.

*Sepals*.—Shape: overall shape is generally lanceolate with an acute apex and truncate base. Upper surface: covered with short pubescence, and commonly near Green Group 143C in coloration. Under surface: commonly puberulent, and commonly near Green Group 143A in coloration. Size: commonly approximately 2.4 cm in length on average, and approximately 7 mm in width at the base. Margin: entire, and commonly with an extension on two or three of the sepals measuring approximately 6 mm in length on average and approximately 1 mm in width on average. Number: five.

*Petaloid*.—Number: commonly approximately 1 to 2 on average. Length: approximately 2.0 cm on average. Width: approximately 1.5 cm on average. Shape: oval. Color: commonly near Yellow-Orange Group 23B.

*Buds*.—Shape: generally ovoid. Length: approximately 2 cm on average as the calyx breaks. Diameter: approximately 1.2 cm on average as the calyx breaks. Color: near Red Group 37A towards the apex.

*Flower*.—Form: single, cuplike. Diameter: commonly approximately 6 cm on average when fully open. Depth: commonly approximately 4.0 cm on average. Color (when opening begins): Upper surface: near Yellow-Orange Group 17A at the point of attachment, transitioning to near Orange Group 29B at the apex. Under surface: near Yellow-Orange Group 21B at the point of attachment blending to Red Group 37A at the apex. Color (at end of blooming): Upper surface: near Yellow Group 5A at the point of attachment, transitioning to Red Group 36A at the apex. Under surface: near Yellow-Orange Group 18A at the point of attachment blending to near Red Group 38C at the apex. Fragrance: slightly sweet. Petal number: commonly approximately 8 to 10 on average under normal growing conditions. Petal length: commonly approximately 3 cm on average.

Petal width: commonly approximately 3.5 cm on average. Petal shape: broadly obovate. Petal margin: entire. Petal apex: slightly cuspidate. Petal base: cuneate. Petal upper surface basal spot: small. Petal drop: good, the petals commonly detach cleanly and freely drop upon full maturity. Stamen number: approximately 80 on average. Anthers: commonly near Yellow Group 13A in coloration. Filaments: approximately 7 mm in length, and the coloration is near Yellow Group 13C. Pollen: commonly present in a moderate quantity, and near Yellow-Orange Group 20A in coloration. Pistils: separate and free, and commonly number approximately 35 on average. Styles: commonly approximately 1 cm in length and near Red-Purple Group 60A at the tip and near Yellow-Green Group 145C at the base. Stigma: commonly less than 1 mm in diameter, and near Greyed-Yellow Group 162B in coloration. Receptacle: commonly substantially round in shape, approximately 8 mm in diameter, smooth in texture, near Yellow-Green Group 144A in coloration, and with achenes commonly being present on the bottom and wall. Hips/seeds: commonly present in moderate quantity.

Development:

*Vegetation*.—Dark green vigorous, and strong.

*Blossoming*.—Abundant and substantially continuous from spring to frost.

*Lastingness of flowers*.—A bloom commonly stays on the plant for approximately 4 to 5 days on average.

*Resistance to diseases*.—Excellent, particularly with respect to black spot (*Diplocarpon rosae*), rust (*Phragmidium*), and mildews.

Plants of the 'Radnectar' variety have not been observed under all possible environmental conditions to date. Accordingly, it is possible that the phenotypic expression may vary somewhat with changes in light intensity and duration, cultural practices, and other environmental conditions.

I claim:

1. A new and distinct Grandiflora rose plant characterized by the following combination of characteristics:

(a) abundantly and substantially continuously forms attractive single cup-shaped bright orange to apricot blossoms, (b) exhibits an upright and bushy growth habit, (c) forms vigorous vegetation, (d) forms attractive ornamental dark green foliage with a glossy finish on the upper surface that contrasts well with the blossom coloration, (e) exhibits excellent disease resistance particularly with respect to black spot, rust and mildews, and (f) is well suited for providing attractive ornamentation in the landscape;

substantially as herein shown and described.

* * * * *